(12) United States Patent
Corbellini et al.

(10) Patent No.: US 10,758,024 B2
(45) Date of Patent: Sep. 1, 2020

(54) REFILLABLE PACKAGE FOR A FROZEN PERSONAL CARE PRODUCT

(71) Applicant: ELC Management LLC, Melville, NY (US)

(72) Inventors: Francis Corbellini, Thiais (FR); Herve F. Bouix, New York, NY (US)

(73) Assignee: ELC MANAGEMENT LLC, Melville, NY (US)

( * ) Notice: Subject to any disclaimer, the term of this patent is extended or adjusted under 35 U.S.C. 154(b) by 432 days.

(21) Appl. No.: 15/833,294

(22) Filed: Dec. 6, 2017

(65) Prior Publication Data
US 2019/0166973 A1 Jun. 6, 2019

(51) Int. Cl.
| | | |
|---|---|---|
| *A46B 11/00* | (2006.01) |
| *A45D 33/26* | (2006.01) |
| *A45D 34/04* | (2006.01) |
| *A45D 40/00* | (2006.01) |
| *A61Q 19/00* | (2006.01) |

(52) U.S. Cl.
CPC .............. *A45D 33/26* (2013.01); *A45D 34/04* (2013.01); *A45D 40/00* (2013.01); *A45D 2200/05* (2013.01); *A61K 2800/84* (2013.01); *A61Q 19/00* (2013.01)

(58) Field of Classification Search
CPC .. A45D 40/0087; A45D 40/28; B65D 75/367; B65D 75/527
USPC ........................................................ 401/130
See application file for complete search history.

(56) References Cited

U.S. PATENT DOCUMENTS

| | | | |
|---|---|---|---|
| 2,946,207 A | 7/1960 | Hulterstrum | |
| 4,378,025 A | 3/1983 | Gaston | |
| 7,097,626 B2 * | 8/2006 | Louis | A61H 7/003 601/135 |
| 7,478,962 B2 * | 1/2009 | De Laforcade | A45D 40/0087 401/202 |
| 8,777,504 B2 * | 7/2014 | Shaw | A61B 90/70 401/202 |
| 8,783,451 B2 * | 7/2014 | Slokovic | A61P 17/02 206/209 |

FOREIGN PATENT DOCUMENTS

WO WO-2008-131804 A1 11/2008

OTHER PUBLICATIONS

ISR and WO of corresponding PCT application: US2018/063889.

* cited by examiner

*Primary Examiner* — Jennifer C Chiang
(74) *Attorney, Agent, or Firm* — Peter Giancana

(57) ABSTRACT

A refillable unit dose package for frozen cosmetic or personal care products that can provide a chilling effect during application. The main components of the package are a reservoir and an applicator. The applicator comprises a handle and an applicator head depending from the handle. In use, a product in the reservoir is frozen, which causes the product to bond to the applicator head. The handle is used to lift the frozen product out of the reservoir, and draw the frozen product over the skin. As it melts from the heat of the skin, the product can be spread on the skin. The reservoir is refillable by a consumer.

5 Claims, 12 Drawing Sheets

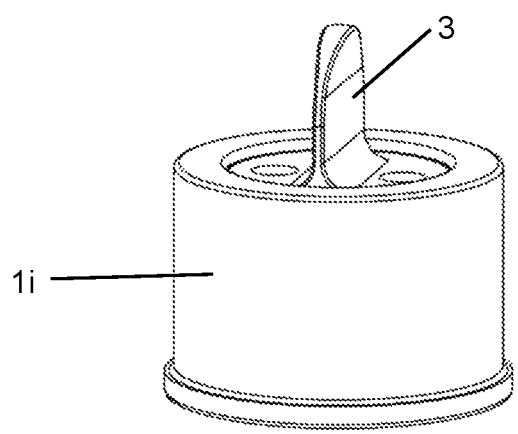
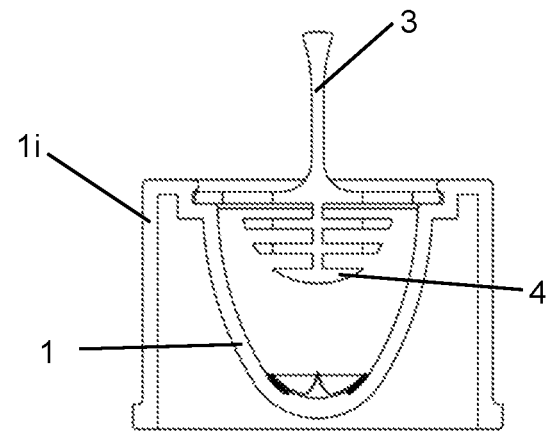
FIG. 7A
FIG. 7B
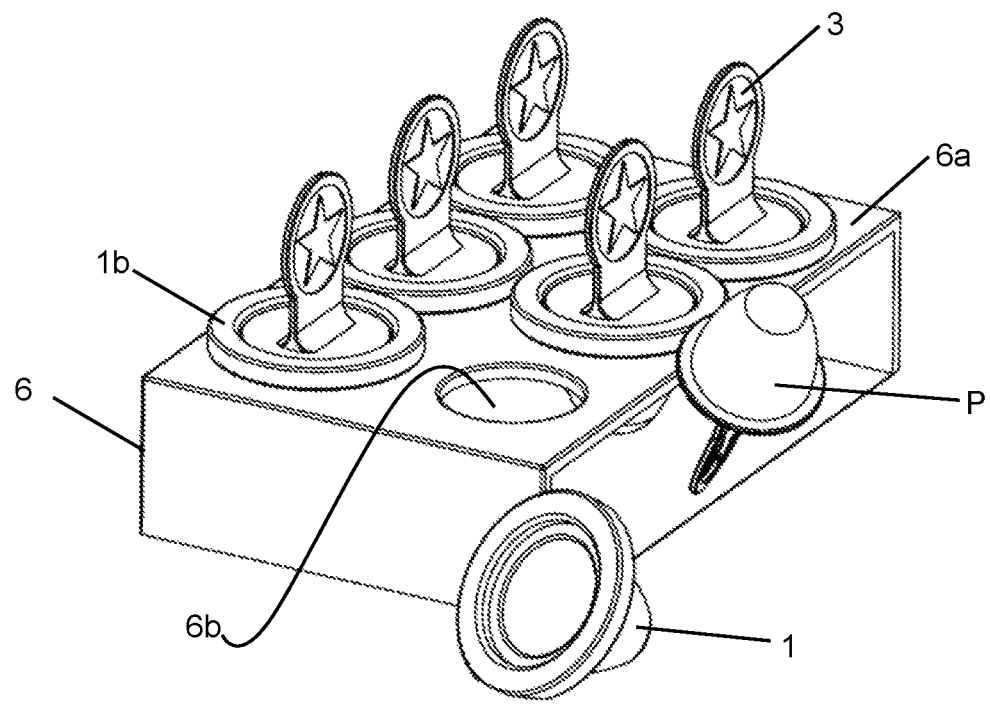
FIG. 8

REFILLABLE PACKAGE FOR A FROZEN PERSONAL CARE PRODUCT

FIELD OF THE INVENTION

The invention is in the field of unit dose packaging for cosmetic or personal care products. More specifically, we disclose a refillable package that is designed to house and apply frozen personal care products that are able to provide a chilling effect during application.

BACKGROUND OF THE INVENTION

For the convenience of the cosmetic user, cosmetic packaging often includes an applicator that is suitable for dispensing the particular cosmetic contained in the package reservoir. The applicator head or applicator tip is used to apply and spread the applied product, and may additionally serve to massage the skin of the user in the application area. It is also believed that cooling the skin can have a beneficial effect. For example, cooling the skin area below the eyes has been shown to reduce puffiness. In the past, applicator heads and applicator tips having a variety of shapes and configurations have been provided with means for cooling, but the effectiveness has generally been limited by the relatively small thermal mass of the components and by other limitations. Alternatively, pre-chilled creams or lotions, or chilled washcloths or cleansing pads have been used to reduce skin temperature, but not necessarily in convenient, single does forms, and the product, while chilled, may provide only a limited cooling effect. In contrast, a frozen product can deliver a much more significant chilling effect to the skin, than a merely chilled product or product applicator.

U.S. Pat. No. 4,378,025 describes cosmetic products in the form of deep-frozen blocks or cakes, which are directly applicable to the skin. The relatively large blocks are molded around supports (sticks for example) made from wood, plastic material, whose ends projecting from the block will enable them to be easily handled. A user is able to withdraw the deep-frozen block from its mold without contact with the cosmetic substance. The process for packing the described blocks consists in pouring or compressing the cosmetic substance in a mold, and in cooling the substance rapidly and intensively to a complete deep-freeze, i.e. between −25° C. and −80° C. The relatively large blocks allow multiple applications with the block being returned to a freezer for storage between uses. A drawback of the '025 invention is the need to remove the entire block of cosmetic product from the freezer. Now, the block is so large such that, in a single application, only a small portion of the surface of the bock will ever contact the skin. The result is that some product near the surface of the block melts, but is not deposited on the skin. The amount of melting may be significant if the product block spends several minutes or longer out of the freezer. Subsequently, this melted product is returned to the freezer, thus being subject to at least one freeze thaw cycle (and probably several freeze thaw cycles) before it will actually be applied to a user's skin on some future application. On the one hand, the portion of product that was subject to at least one freeze thaw cycle may be degraded in appearance, or texture, or efficacy of its active ingredients or any combination thereof. Clearly then, thawing and refreezing any amount of the product should be avoided. On the other, depending on its melting point temperature and consistency, the melted product that does not get deposited on the skin may run down the handle or onto the hand of the user, or otherwise drip and create a messy situation.

Accordingly there is a need for refillable unit dose packaging for cosmetic or personal care products wherein the package is designed to house and apply a single dose of frozen cosmetic or personal care products that can provide a significant chilling effect during application, while avoiding degradation of the product due to freeze-thaw, and avoiding the other problems described above.

SUMMARY OF THE INVENTION

The main components of the invention are a refillable reservoir and an applicator. The applicator comprises a handle and one or more applicator heads depending from the handle. The surface of the applicator head is contoured, embossed and/or dimpled. When not in use, the reservoir houses a personal care product and an applicator head. In use, a product in the reservoir is frozen, which causes the product to bond to the applicator head. The handle is used to lift the frozen product out of the reservoir, and draw the frozen product over the skin. As it melts from the heat of the skin, the product can be spread on the skin. Once all or enough product has melted off of the applicator head, the contoured surface of the applicator head contacts the skin, and is able to provide one or more effects, such as a massage effect, an exfoliation effect, an effect of driving active ingredients into the skin, etc. The empty reservoir may be refilled with non-frozen, flowable product, and subsequently frozen for later use. In some embodiments, the reservoir is designed to stand upright on its base, while in other embodiments, one or a set of more than one reservoir is held in a tray.

DESCRIPTION OF THE FIGURES

FIGS. 1A-7B depict various embodiments of a product reservoir (1) according to the invention.

FIGS. 8-11 depict various embodiments of a tray (6) that holds multiple reservoirs (1).

DETAILED DESCRIPTION

The Reservoir

The first main and essential component of the invention is a reservoir (1) that is able to be filled with and retain a personal care product (P) that is a liquid or semi-liquid at standard atmospheric pressure and temperature, and that freezes at lower temperatures. Many types of personal care products will freeze at temperatures substantially close to 0° C., but those that freeze at higher or lower temperatures may also be useful. The reservoir should be able to withstand product expansion and contraction without rupturing. It should also be non-reactive with the products that it is intended to hold. To that end, reservoirs of the invention may be fashioned out of elastic materials, such as thermoplastic elastomers or silicone rubbers. The reservoir components described herein, may be fashioned from these materials by various molding techniques, such as injection molding.

Figure 1A:
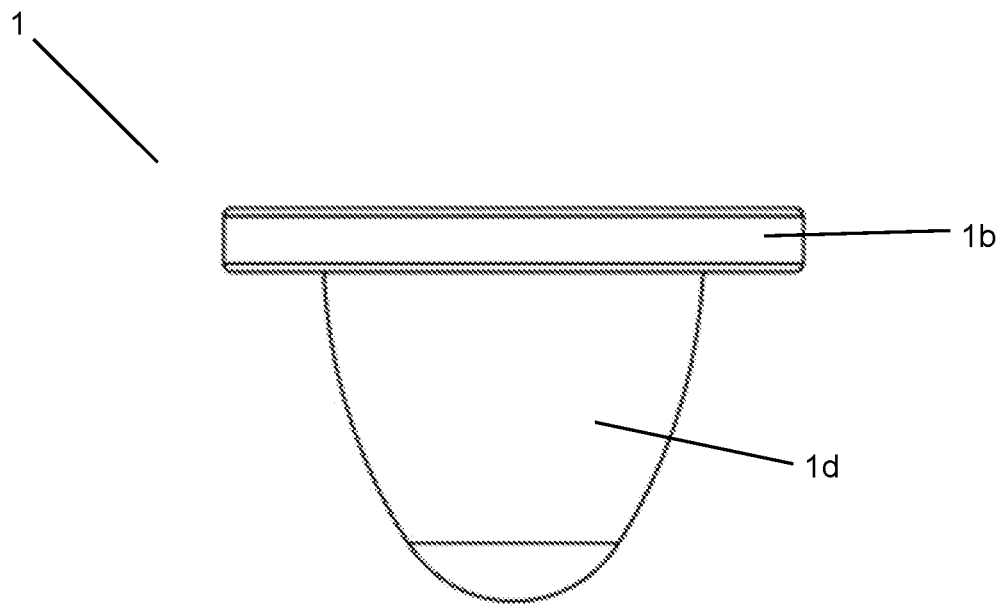
Figure 1B:
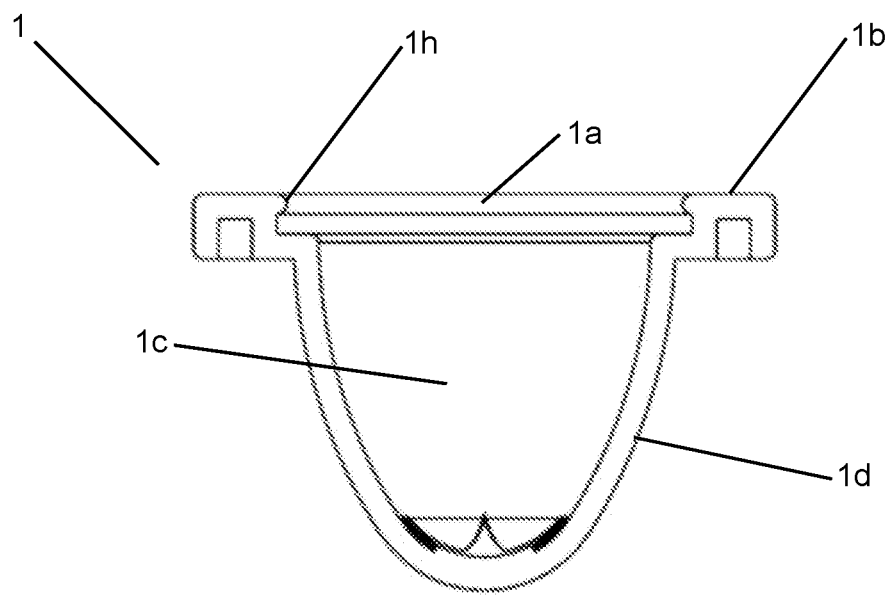
Figure 2:
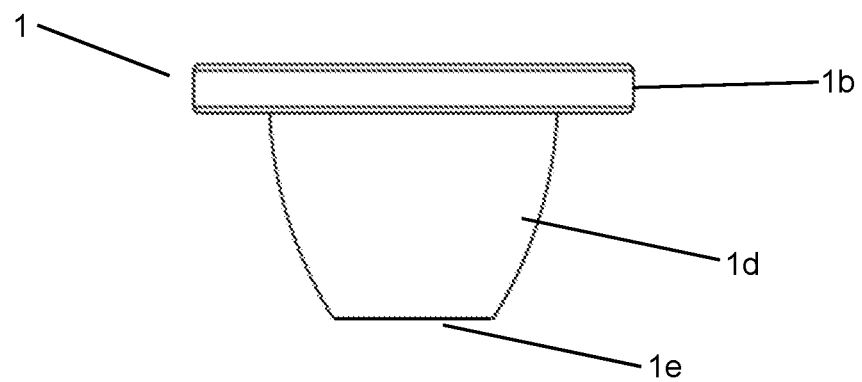

Referring to FIGS. 1A and 1B, a preferred set of embodiments of the reservoir (1) comprises a wall (1d) and a perimeter (1a) that defines an opening in the wall. Generally, the opening in the wall occurs where the cross sectional diameter of the wall is at its greatest. This allows the frozen product to be withdrawn from the reservoir. The perimeter extends outwardly into a flange (1b). The reservoir comprises an interior space (1c) that is defined by the wall. All or a portion of the wall (1d) of the reservoir may be opaque, translucent or transparent.

The interior space (1c) of the reservoir (1) has a volume that is occupied by a personal care product (P), as well as the applicator head (4) of an applicator (2) according to the present invention. The amount of volume taken up by the personal care product is enough for at least one complete application of the product according to its intended use. As an example, in some embodiments, one application of a face product may require from 1 mL to 7 mL, while one application of a body product may require from 7 mL to 20 mL.

Figure 3:
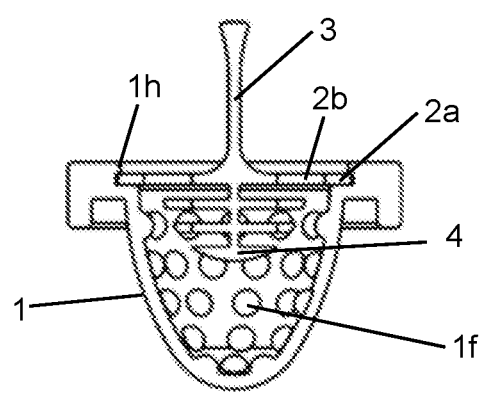
Figure 4:
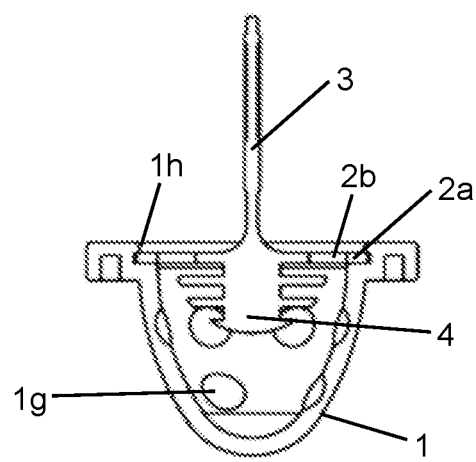
Figure 5:
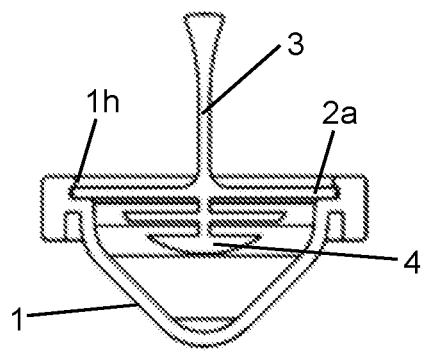
Figure 6:
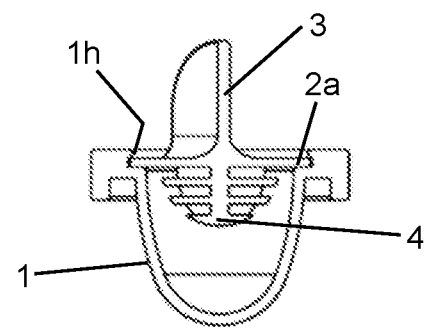
Figure 9:
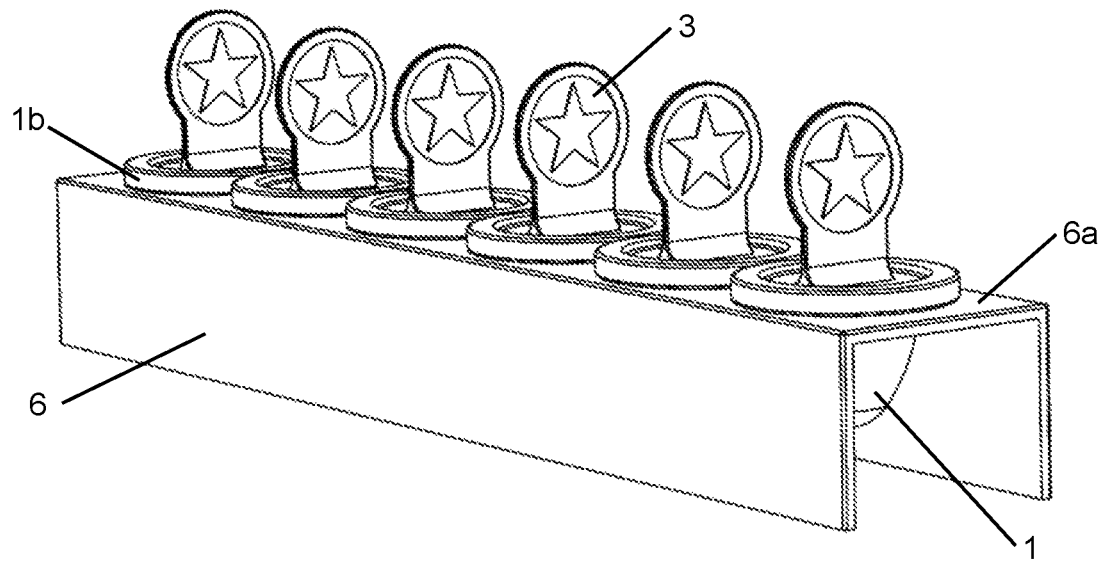
Figure 10:
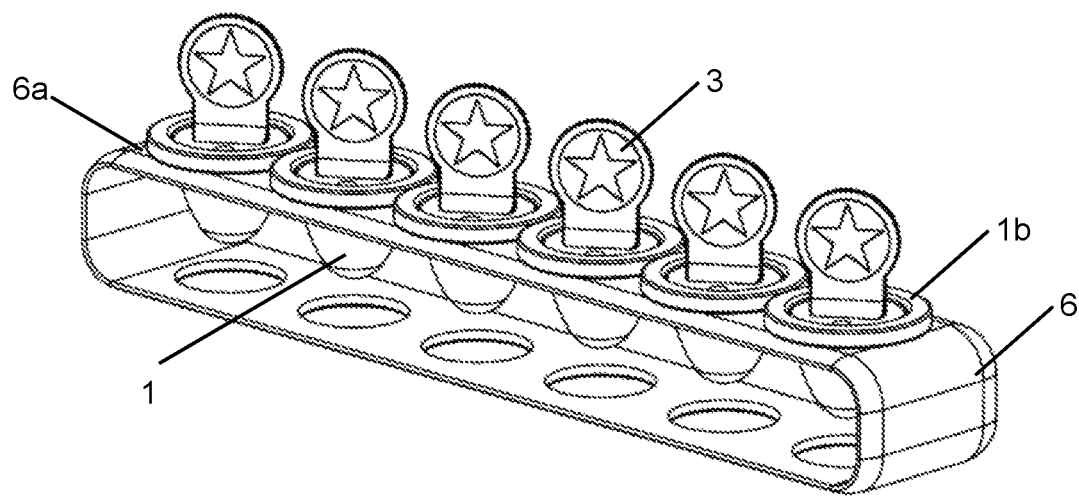
Figure 11:
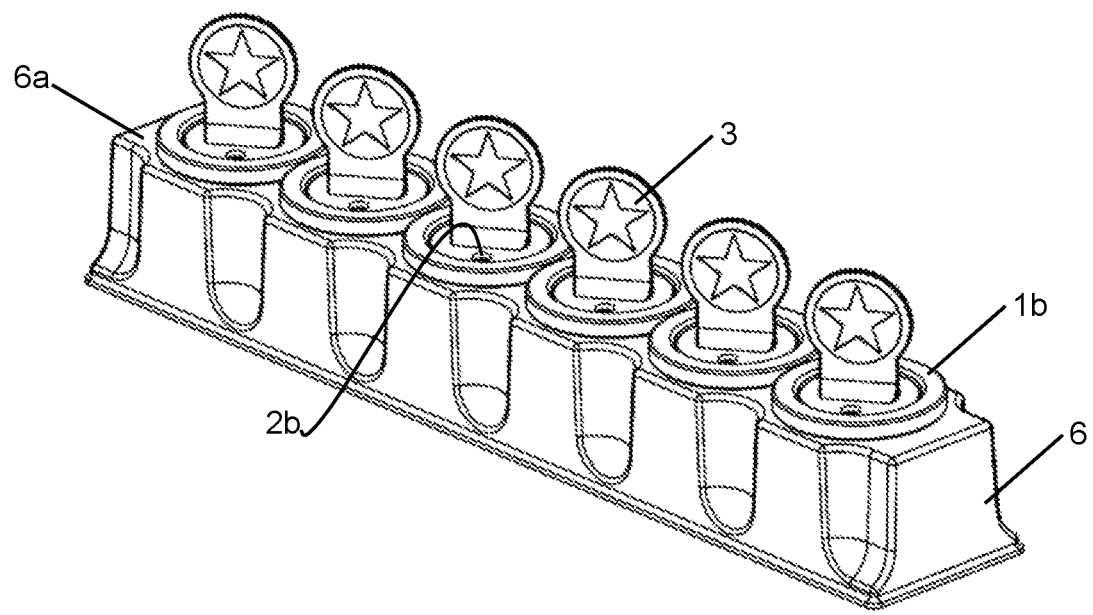
Figure 12:
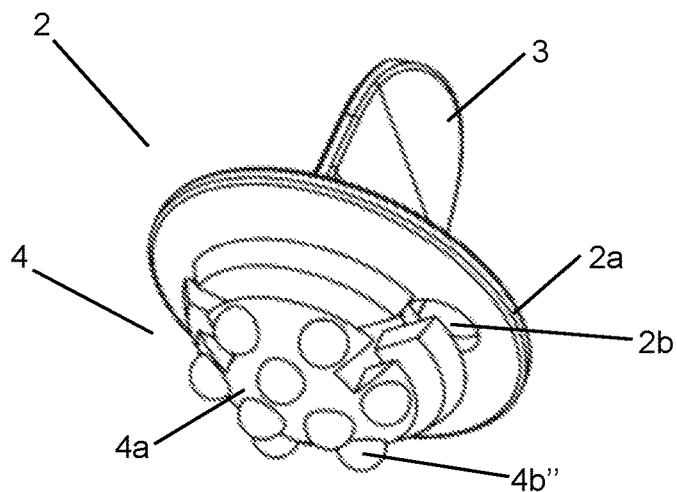
FIGS. 12-20 depict various embodiments of molded applicators (2) that comprise a handle (3) and an applicator head (4), and that is designed to be used with the reservoir (1).
Figure 13:
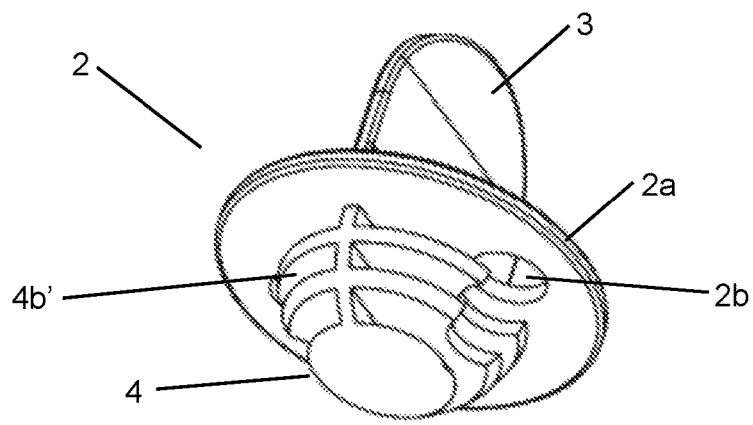
Figure 14:
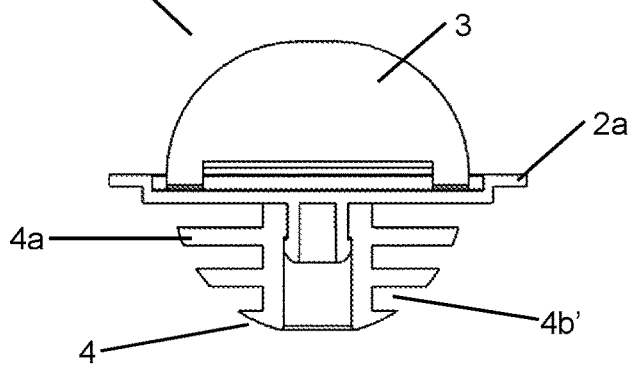
Figure 15:
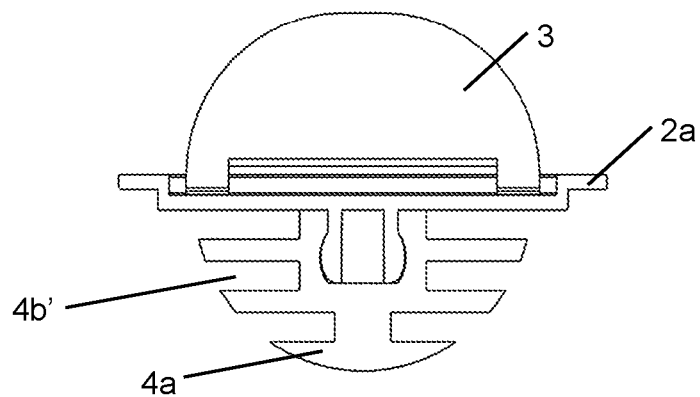
Figure 16:
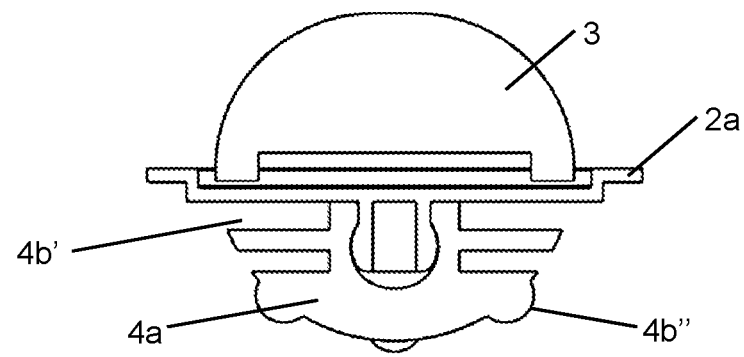
Figure 17:
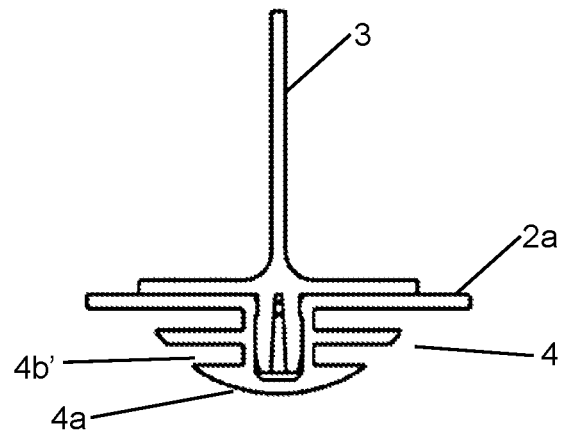
Figure 18:
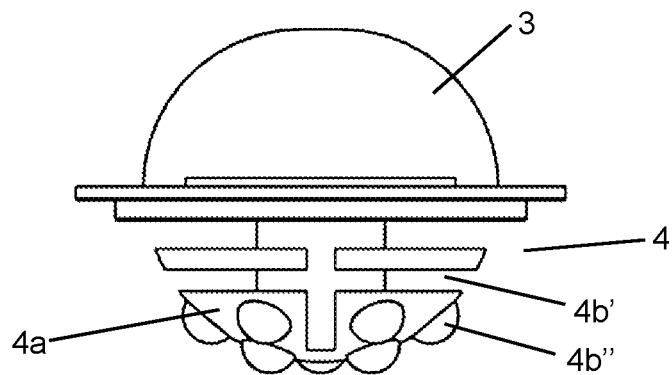
Figure 19:
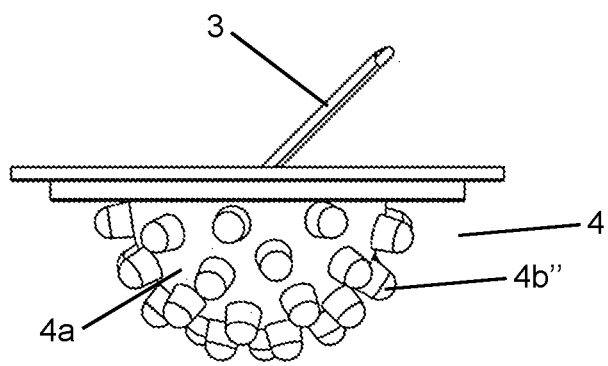
Figure 20:
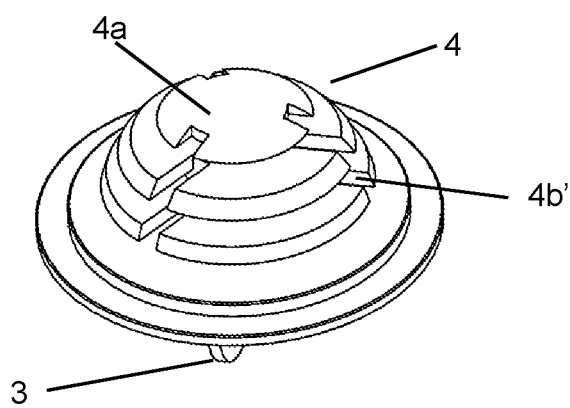

FIGS. 1A to 6 depict non-exhaustive variations of the reservoir (1). The interior surface of the wall (1d) of the reservoir (1) should be free of surface features that would significantly inhibit the removal of the frozen personal care product from the reservoir. On the other hand, any surface features embossed or engraved on the interior surface of the wall of the reservoir would produce complementary features on the surface of the frozen product. Such surface features on the frozen product are optional, but may be desirable. Examples of embossed or engraved features on the interior surface of the wall of the reservoir are shown in FIGS. 3 and 4. For example, the interior wall of the reservoir of FIG. 3 is provided with a number of embossed circular features (1f) that will give rise to indentations on the surface of the frozen product. In FIG. 4, the interior wall is provided with engraved circular indentations (1g) that will give rise to raised dimples on the surface of the frozen product. Another type of surface feature is an assortment of flat facets (1j, see FIG. 21C), which add contour and a stylish look to the frozen product. Combinations of embossed and engraved features in an unlimited number of shapes and sizes are also possible.

Preferably, one or multiple reservoirs (1) according to the invention are able to be maintained in an upright position, such that non-frozen product in the reservoir will not leak out of the reservoir. For example, the reservoir may be provided with a flattened base (1e) (see FIG. 2, for example). Alternatively, each reservoir itself, may comprise a cylindrical outer wall (1i) that projects downwardly from the flange (see FIGS. 7A and 7B). The wall extends beyond the bottom of the reservoir, so that the base of the cylindrical wall provides a stable footing for the reservoir, so that it will not tip over. In other embodiments one or more reservoirs are held in a tray (6). Several embodiments of a tray are shown in FIGS. 8-11. The tray comprises a raised platform (6a) with two or more openings (6b). Reservoirs (1) are disposed in the openings, and the flange (1b) of the reservoir rests on the raised platform, such that the reservoir is maintained in an upright position. The tray may be in any shape or size, and may contain any number of openings to accommodate multiple reservoirs. The tray may be plastic or metal, and should be suitable for storage in a freezer over a period of days, weeks or months without breaking.

The Applicator

The applicator (2) comprises a handle (3) and one or more applicator heads (4) depending from the handle. The handle is an elongated part of the applicator that is grasped by a user during intended use of the package. A typical handle is large enough to be firmly grasped between the thumb and pointer finger, such that the applicator can be drawn across the surface of the skin without difficulty. The handle may be any convenient shape, such as a rectangular or semi-circular. Also, the handle is preferably rigid which increases control of the applicator during use. The handle will typically be molded in a sufficiently stiff plastic.

The applicator head (4) depends from the handle (3), and is designed to hold the frozen personal care product (P). For ease of application, the connection between the handle and applicator head is preferably rigid. To this end, the applicator head and handle may be integrally molded out of one material, as in FIGS. 3-6. Alternatively, the applicator head and handle may be fashioned separately out of the same or different material, and later joined together. Means of joining may include friction or snap fit as shown in FIGS. 14-17, as well as adhesive and welding. FIGS. 12-17 depict stiff, plastic molded applicator heads, while sponge embodiments are discussed further below.

The bare applicator head (4) is small enough to fit into the reservoir (1), as shown in FIGS. 3-6. By "bare applicator head" we mean an applicator head (4) that has little or no product (P) adhered to it, either because the applicator head has not yet been immersed in a product reservoir (1), or because the product has been depleted from the applicator head, creating bare spots that are able to contact the skin of a user. To ensure that the frozen product (P) adheres to a bare applicator head (4), the outer surface (4a) of an applicator head is provided with contours and/or textural features that are able to increase the adherence of the frozen product to the bare applicator head. Examples of textural features include depressions, such as dimples and grooves (4b'), and/or elevations, such as raised bumps (4b"), as shown in the non-limiting examples of FIGS. 12-20. The applicator head may have any combination of such textural features in varying numbers.

The applicator (2) may further comprise a sealing disk (2a) that is sandwiched between the handle (3) and the applicator head (4), and that is sized to fit snugly against the perimeter (1a) of the reservoir (1). The sealing disk helps to seal the reservoir and contain the product prior to use. The sealing disk may be molded separately from the handle (3) and applicator head (4), and sandwiched between them during assembly (as in FIGS. 14-16). Alternatively, the sealing disk may be integrally molded with either one of those. For example, in FIGS. 12-13, the sealing disk is integral with the handle, while in FIG. 17, it is integral with the applicator head (4). The shape of the perimeter of the sealing disk matches the shape of the perimeter (1a) of the reservoir. The two perimeters may be sized for an interference fit of the sealing disk in the reservoir. This interference is enough to seal the product in the reservoir from the ambient environment, but not so tight that a user cannot pull the applicator out of the reservoir, that is to say, the sealing disk is removable by a user. Optionally, the perimeter (1a)

of the reservoir may be fashioned as a flexible annular bead (1*h*). The diameter of the annular bead is a little smaller than the diameter of the sealing disk. The sealing disk may be forced under the annular bead by which the sealing disk is held in place (see FIGS. 3-6). The flexibility allows the sealing disk to be lifted from the reservoir by a user.

Figure 21A:
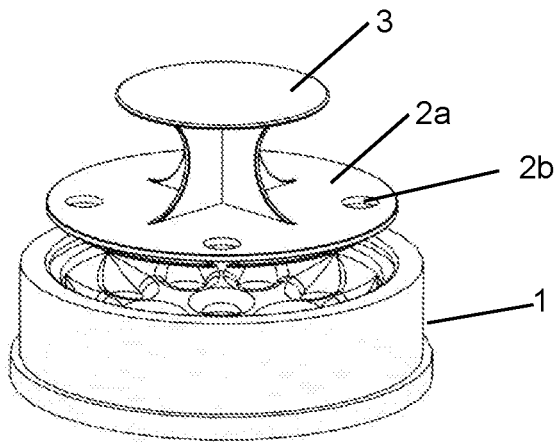
FIGS. 21A, 21B and 21C show one preferred embodiment of a refillable package for a frozen personal care product.
Figure 21B:
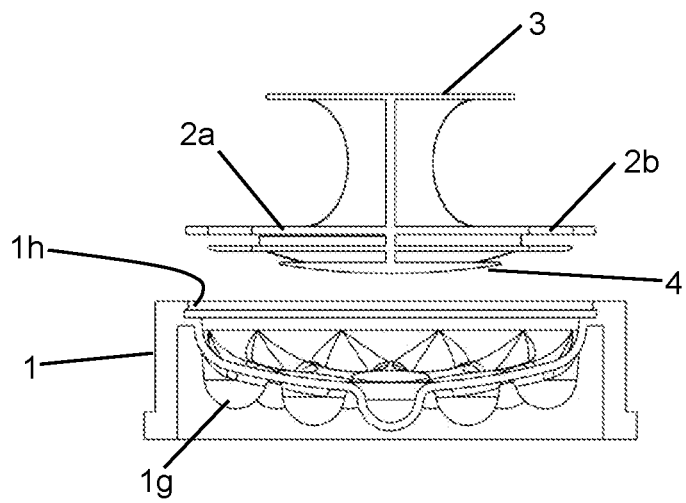
Figure 21C:
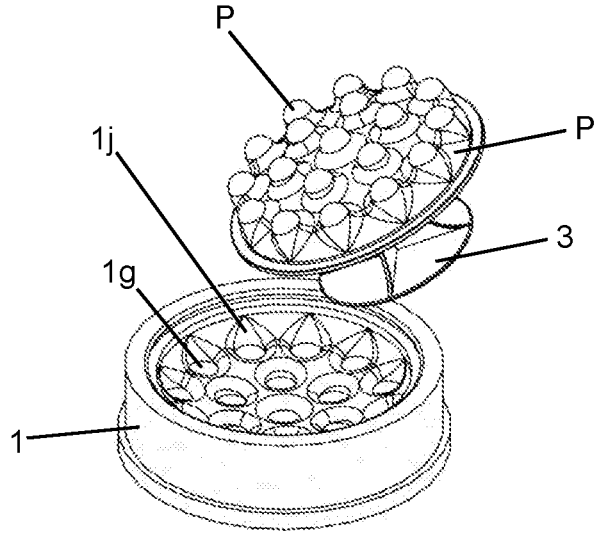

One preferred package according to the invention is shown in FIGS. 21A-C. In this embodiment, the reservoir (1) is shallower and wider compared to those depicted in FIGS. 1A to 6. Consequently, a personal care product (P) that is frozen in this reservoir will have a wider and flatter surface area to present to the skin of a user. When, as shown in FIGS. 21A-C, the reservoir is also provided with a multitude of indentations (1*g*), then the frozen product (see FIG. 21C) will feature a multitude of raised dimples that are able to contact the skin simultaneously, and provide a massaging effect, while applying product.

Optionally, the sealing disk (2*a*) is provided with an opening (2*b*) that leads into the reservoir (1), through which the reservoir can be filled even when the sealing disk is seated against the perimeter (1*a*) of the reservoir. Embodiments with an opening in the sealing disk are shown in FIGS. 3, 4, 7A, 7B, 11-13, 21A-C, and 22A-C.

Figures 22A, 22B, 22C:
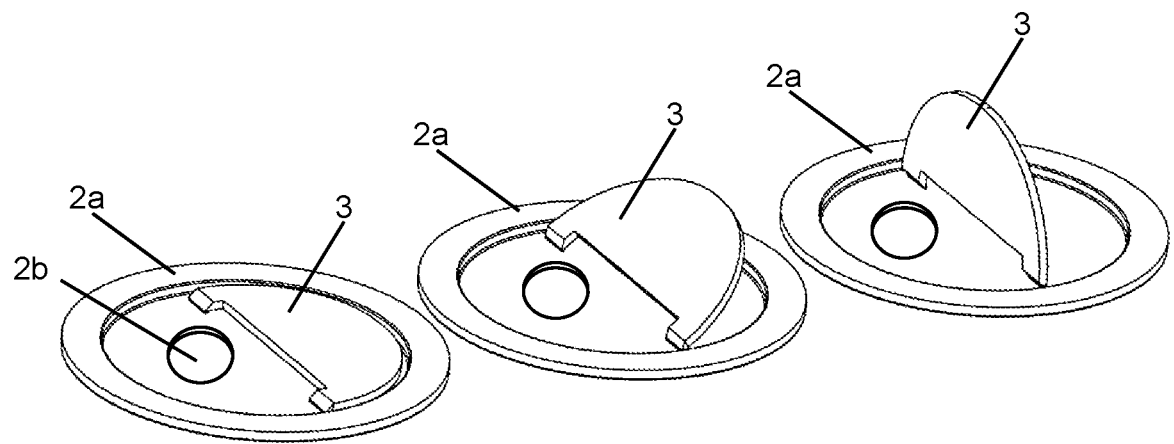
FIGS. 22A, 22B and 22C show one embodiment of the sealing disk (2a) wherein a handle (3) is attached to the sealing disk by hinge mechanism.

Optionally, but preferably, the handle (3) is able to lie flat. In FIGS. 22A, 22B and 22C, the handle is attached to the sealing disk (2*a*) by a hinge mechanism, such as a living hinge molded at the joining of the handle and sealing disk. When not in use, the handle lies flat against the sealing disk, but can be rotated 90° use. Other than a living hinge, the handle and sealing disk may be separately molded and joined with any suitable sort of pinned hinge mechanism.

Figure 23A:
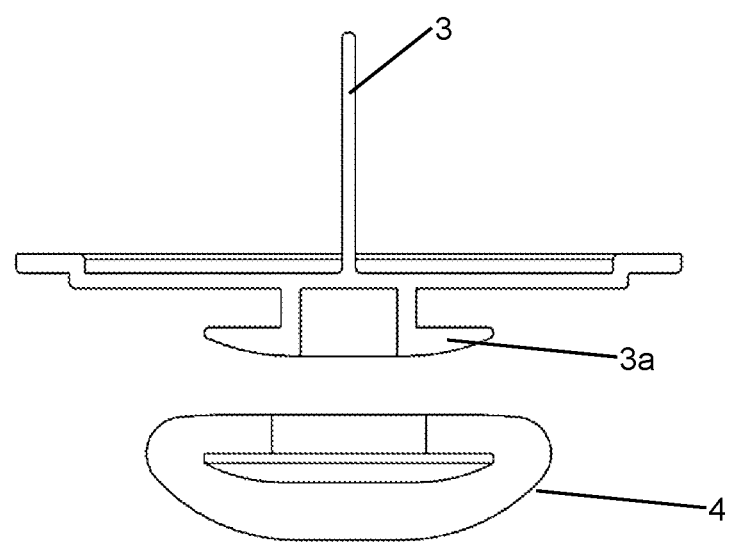
FIGS. 23A, 23B, 24 and 25 depict sponge applicator heads (4), and various means of attaching the applicator heads to the handle (3).
Figure 23B:
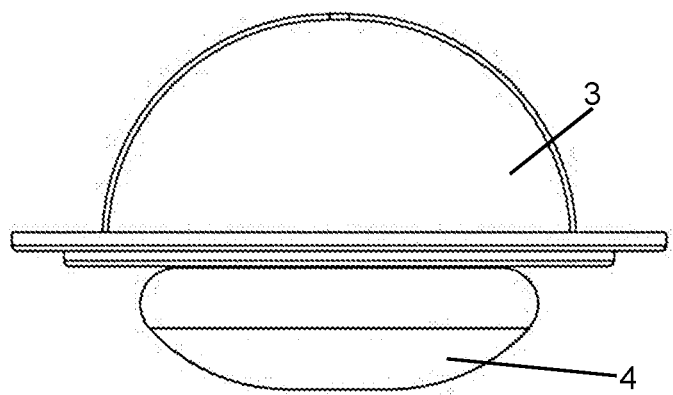
Figure 24:
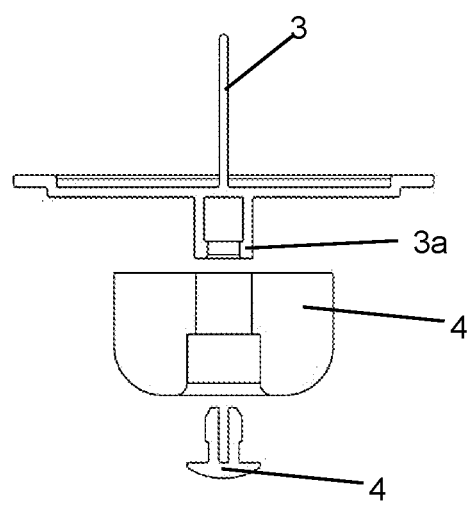
Figure 25:
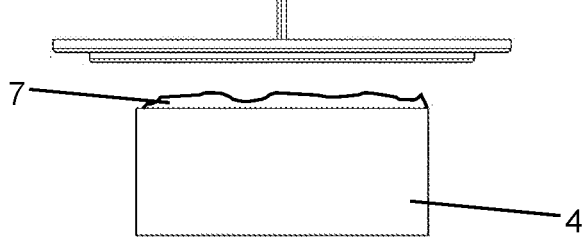

The applicator head (4) may be a plastic or elastomer molded surface as shown in FIGS. 2-7, 12-20 and 21B. Alternatively, the applicator head may comprise one or more sponges. Some embodiments are shown in FIGS. 23A-25. In FIGS. 23A and 23B, a sponge applicator head (4) stretches around a stem (3*a*) of the handle (3). In FIG. 224, a sponge that has a central bore is mounted to a stem (3*a*) of the handle (3) and held in place by a pin (4*d*), as shown. The pin is retained in the stem by a snap or friction fitting. In FIG. 25, a sponge applicator head (4) is attached to a handle (3) by adhesive (7). Other means, such as welding, may also be used to affix the applicator head to the handle. Also contemplated are applicator heads that comprise at least one molded plastic section and at least one sponge section.

The Product

The unit dose package of the present invention is designed to house and apply frozen cosmetic or personal care products. A reservoir (1) according to the invention, as described above, is filled with a product (P) that is non-solid when dispensed into the reservoir. Such product types include liquids, semi-liquids, gels, creams, lotions, pomades, etc. At the time of filling into the reservoir, the product must be sufficiently soft to allow a bare applicator head (4) to penetrate into the product, and sufficiently flowable to enclose around the applicator head and make continuous contact with the applicator head. The product in the reservoir must have a freezing point of no lower than −20° C., preferably no lower than −15° C., more preferably no lower than 0° C.

Filling and Using

A package according to the present invention can be sold empty, or the package may be sold with product already in the reservoir (1), having been filled at the factory. When the reservoir (1) is filled at the factory, the reservoir will be filled by any means known in the field of personal care products, such as being dispensed under pressure through a filling nozzle. Whether the reservoir is sold filled or empty, a supply of product (P) will be separately provided so that the consumer can fill the reservoir as needed. The separately supplied product is flowable, and may be dispensed into the reservoir from a container (9), such as by pouring from a bottle, squeezing from a tube or by some other means. Typically, the product (P) to be filled will be in a liquid state, at a temperature well above the freezing point of the product. Preferably, the amount of product in one reservoir is sufficient for only a single use.

Figure 26:
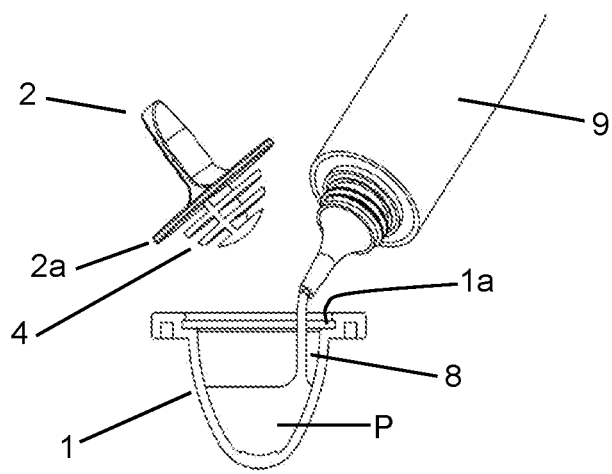
FIG. 26 depicts a reservoir (1) being filled before the applicator (2) is mounted to the reservoir.

Whether in the factory or in the home, the reservoir may be filled before the applicator (2) is mounted to the reservoir (see FIG. 26). In this case, once the reservoir is filled with non-solid product (P), the bare applicator head (4) of an applicator is inserted into the non-solid product until the sealing disk (2*a*) fits snugly against the perimeter (1*a*) of the reservoir. One disadvantage of this filling method is that if too much product is filled into the reservoir, then product will overflow the reservoir when the applicator head is inserted into the product. To alleviate this problem, a marking, such as a fill line (8), could be provided on the wall of the reservoir.

Figure 27:
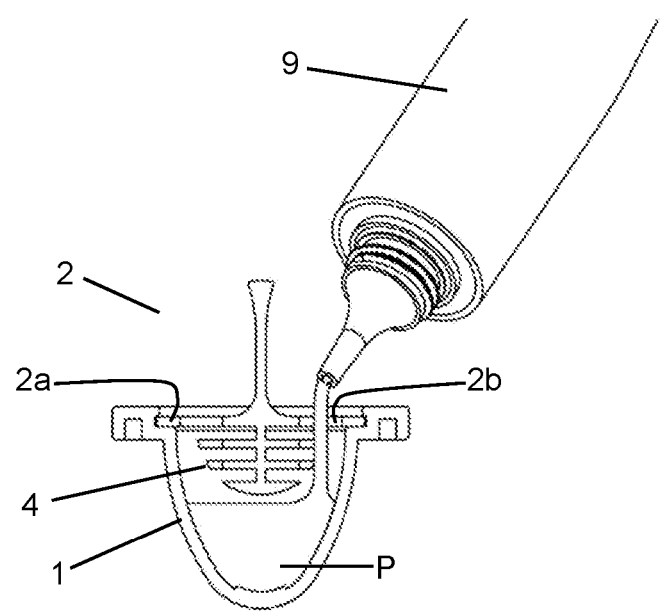
FIG. 27 depicts a reservoir (1) being filled through an opening (2b) in the sealing disk (2a), after the applicator (2) is mounted to the reservoir.

Alternatively, if the sealing disk (2*a*) is provided with an opening (2*b*), then the reservoir (1) may be filled after the applicator (2) is mounted to the reservoir. In this case, the sealing disk (2*a*) is secured to an empty reservoir. Flowable product (P) is filled into the reservoir through the opening in the sealing disk (see FIG. 27). This filling method is preferred because with the applicator head (4) already in the reservoir, it is easy to ensure than the reservoir is not overfilled.

If the reservoir is filled in the factory, before distribution to consumers, then the opening (2*b*) in the sealing disk (2*a*) should be covered to prevent contamination. An adhesive backed substrate, such as a paper label or foil label may be used for this purpose, or a removable plug. In this case, there is no need to immediately freeze the filled packages. Generally, the filled and sealed reservoirs (1) may be shipped at ambient temperatures, so that the product (P) in the reservoirs is not frozen. When a consumer intends to use the product, she will have to store the filled reservoirs in a freezer for a time sufficient to freeze the product. Upon freezing, the product will adhere to the applicator head (4). This greatly simplifies the handling and distribution process, compared, for example, to the disclosure of U.S. Pat. No. 4,378,025, which calls for rapid and intensive cooling to −25° C. to −80° C. at the time of filling, and maintaining the frozen state until use.

On the other hand, when the reservoir (1) is to be filled or refilled by a consumer through the opening (2*b*) in the sealing disk (2*a*), it generally will not be necessary to cover the opening since the filled package will usually be placed in a freezer right away, with little chance of spilling or spoilage. Upon freezing, the product will adhere to the applicator head (4).

Figure 28:
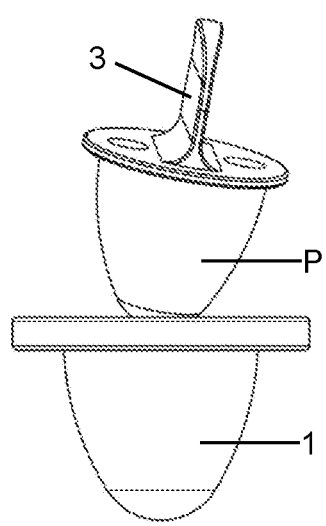
FIG. 28 shows a frozen product (P) being lifted out of a reservoir (1).

When a user wants to apply the product which has previously been frozen, she removes the reservoir (1) from the freezer, grasps the applicator handle (3) and lifts the frozen product (P) out of the reservoir (see FIG. 28). The frozen product is drawn across the skin at those locations where it is desired to be applied. As the surface of the product melts from the heat of the skin, the product is spread onto the skin. Product may be applied until all or most of the product is exhausted. Once all or enough product has melted off of the applicator head, the bare, contoured surface of the applicator head contacts the skin, and is able to provide one or more effects, such as a massage effect, an exfoliation effect, and an effect of driving active ingredients into the skin. Also, the bare applicator head may also be used to smooth, dress up or otherwise work the product as desired. Once application is complete, the applicator and empty reservoir may be discarded, but the present package may be reused again and again, by filling as described above. Alternatively, if not all of the product is used up, and if it has not all melted, then the applicator may be returned to the reservoir for storing in a freezer.

What is claimed is:

1. A unit dose package for a personal care product wherein the package is designed to house and apply a single dose of frozen product that can provide a significant chilling effect during application, the package comprising:
    a reservoir (1) that comprises:
        a wall (1d) that defines an interior space (1c) that has a volume;
        a perimeter (1a) that defines an opening in the wall;
        a flange (1b) that extends outwardly from the perimeter of the opening;
        a cylindrical outer wall (1i) that projects downwardly from the flange (1b), the cylindrical outer wall extending beyond the bottom of the reservoir to provide a stable footing for the reservoir;
        from 1 mL to 20 mL of a personal care product (P) disposed in the interior space (1c) of the reservoir (1), wherein the product is a liquid or semi-liquid at standard atmospheric pressure and temperature, and freezes at no lower than −20° C.; and
    an applicator (2) that comprises:
        a handle (3);
        an applicator head (4) that depends from the handle (3) and that is disposed in the personal care product (P) located in the reservoir (1), and that has an outer surface (4a) with textural features (4b); and
        a sealing disk (2a) that is sandwiched between the handle (3) and the applicator head (4), and that fits snugly against the perimeter (1a) of the reservoir (1), the sealing disk comprising an opening (2b) that leads into the reservoir (1), through which the reservoir can be filled even when the sealing disk is seated against the perimeter (1a) of the reservoir;
    wherein, when the product (P) is frozen, a user is able to grasp the handle (3) and lift the product out of the reservoir.

2. A set of unit dose packages, the set comprising two or more unit dose packages, each unit dose package comprising:
    a reservoir (1) that comprises:
        a wall (1d) that defines an interior space (1c) that has a volume;
        a perimeter (1a) that defines an opening in the wall;
        a flange (1b) that extends outwardly from the perimeter of the opening;
        from 1 mL to 20 mL of a personal care product (P) disposed in the interior space (1c) of the reservoir (1), wherein the product is a liquid or semi-liquid at standard atmospheric pressure and temperature, and freezes at no lower than −20° C.; and
    an applicator (2) that comprises:
        a handle (3);
        an applicator head (4) that depends from the handle (3) and that is disposed in the personal care product (P) located in the reservoir (1), and that has an outer surface (4a) with textural features (4b); and
        a sealing disk (2a) that is sandwiched between the handle (3) and the applicator head (4), and that fits snugly against the perimeter (1a) of the reservoir (1), the sealing disk comprising an opening (2b) that leads into the reservoir (1), through which the reservoir can be filled even when the sealing disk is seated against the perimeter (1a) of the reservoir;
    and a tray (6) that comprises a raised platform (6a) with two or more openings (6b), wherein each reservoir (1) of the two or more unit dose packages is disposed in an opening of the tray, and the flange (1b) of each reservoir rests on the raised platform, such that each reservoir is maintained in an upright position
    wherein, when the product (P) is frozen, a user is able to grasp the handle (3) and lift the product out of the reservoir.

3. A unit dose package for a personal care product wherein the package is designed to house and apply a single dose of frozen product that can provide a significant chilling effect during application, the package comprising:
    a reservoir (1) that comprises:
        a wall (1d) that defines an interior space (1c) that has a volume;
        a perimeter (1a) that defines an opening in the wall;
        a flange (1b) that extends outwardly from the perimeter of the opening;
        from 1 mL to 20 mL of a personal care product (P) disposed in the interior space (1c) of the reservoir (1), wherein the product is a liquid or semi-liquid at standard atmospheric pressure and temperature, and freezes at no lower than −20° C.; and
    an applicator (2) that comprises:
        a handle (3);
        an applicator head (4) that depends from the handle (3) and that is disposed in the personal care product (P) located in the reservoir (1), and that has an outer surface (4a) with textural features (4b); and
        a sealing disk (2a) that is sandwiched between the handle (3) and the applicator head (4), and that fits snugly against the perimeter (1a) of the reservoir (1), the sealing disk comprising an opening (2b) that leads into the reservoir (1), through which the reservoir can be filled even when the sealing disk is seated against the perimeter (1a) of the reservoir;
    wherein the handle (3) is attached to the sealing disk (2a) by a hinge mechanism that enables the handle to lie flat against the sealing disk or be rotated 90°; and
    wherein, when the product (P) is frozen, a user is able to grasp the handle (3) and lift the product out of the reservoir.

4. The unit dose package of claim 3 wherein the outer surface (4a) of the applicator head (4) comprises depressions, such as dimples and grooves (4b'), and/or elevations, such as raised bumps (4b").

5. The unit dose package of claim 3 wherein the applicator head (4) comprises one or more sponges.

* * * * *